United States Patent [19]

King

[11] 4,261,637
[45] Apr. 14, 1981

[54] RECIPROCATING MIRROR DEVICE

[76] Inventor: Bernard G. King, 5 Monmouth Ave., Rumson, N.J. 07760

[21] Appl. No.: 49,961

[22] Filed: Jun. 18, 1979

[51] Int. Cl.³ .......................... A61B 1/24; G02B 7/18
[52] U.S. Cl. ........................................ 350/62; 433/30
[58] Field of Search .................... 350/62, 289; 433/30

[56] References Cited

U.S. PATENT DOCUMENTS

| 2,737,852 | 3/1956 | Porter et al. | 350/62 |
| 3,859,987 | 1/1975 | Holstad | 433/30 |

FOREIGN PATENT DOCUMENTS

| 687620 | 6/1964 | Canada | 350/62 |
| 2143510 | 3/1973 | Fed. Rep. of Germany | 350/62 |
| 364866 | 10/1962 | Switzerland | 350/62 |
| 942100 | 11/1963 | United Kingdom | 433/30 |

Primary Examiner—Jon W. Henry
Attorney, Agent, or Firm—Roger A. Clapp

[57] ABSTRACT

A reflective device for use in a highly moisturized atmosphere is disclosed which comprises a moveable mirror, a housing for holding the mirror and a motor for moving the mirror with sufficient velocity to prevent accumulation of moisture droplets on the surface of the mirror.

1 Claim, 4 Drawing Figures

RECIPROCATING MIRROR DEVICE

BACKGROUND OF THE INVENTION

1. Field of the Invention

This invention relates to small reflective devices and pertains to those which must be used in a highly moisturized ambient.

2. Description of the Prior Art

A dentist's mirror is a typical example of a small reflective device which must be used in a highly moisturized ambient. When used in a patient's mouth, particularly in conjunction with a water cooled high speed drill, a dental mirror rapidly accumulates water droplets until the reflecting surface no longer functions. As a result, the mirror must be exchanged or work stopped until it is dried. The attended delay is both inconvenient and annoying.

Accordingly, the object of this invention is to eliminate the inconvenience and inefficiency caused by water droplets interferring with the reflective capacity of a mirror in a highly moisturized ambient.

SUMMARY OF THE INVENTION

In accordance with this invention, the mirrored surface in a reflecting device is motor driven at a velocity sufficient to retard the accumulation of moisture droplets on the surface thereof.

In accordance with one feature of the invention, the reflective device includes a housing and the mirror portion is rotatably driven by the motor device.

In accordance with another feature of the invention, the motor is driven by fluid stream such as air or the like.

In accordance with another feature of this invention, the motor is driven electromagnetically.

These and other objects and features of the invention will be better understood by reference to the following specification and drawing.

DETAILED DESCRIPTION OF THE INVENTION

Figure 1:
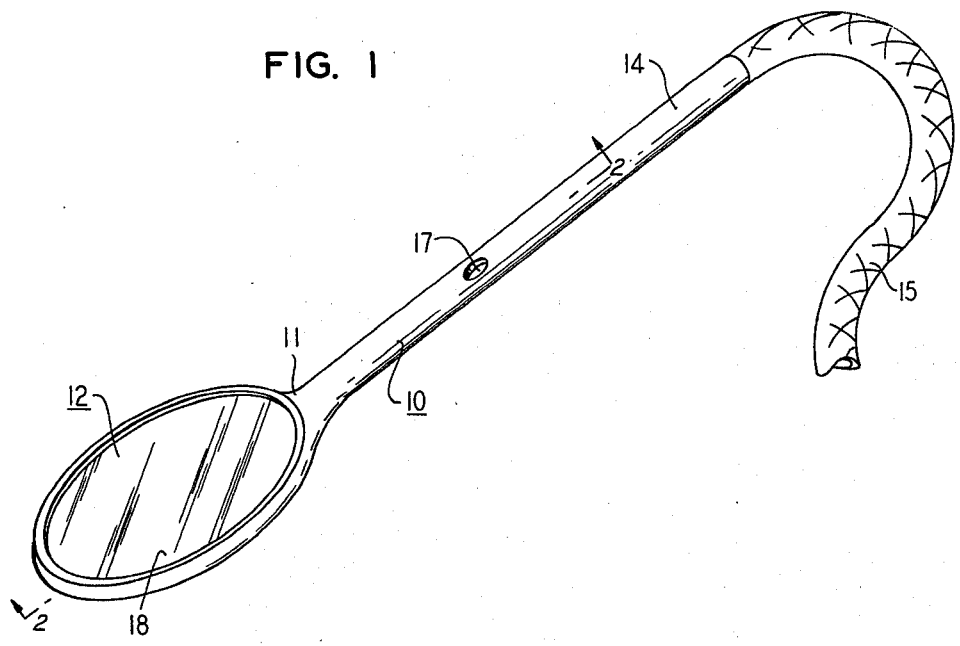
FIG. 1 is a perspective view of a dental mirror constructed in accordance with this invention.
Figure 2:
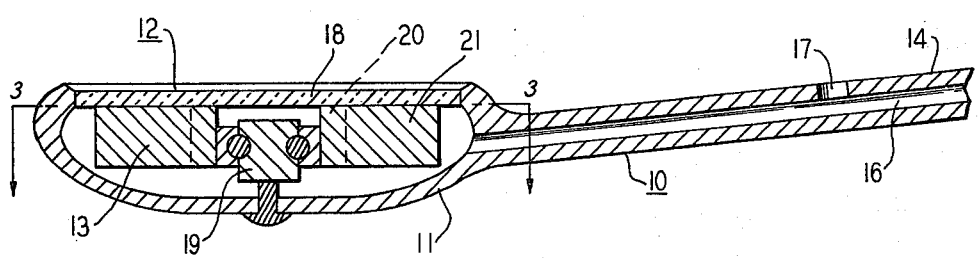
FIG. 2 is a side elevation view of the dental mirror shown in FIG. 1 taken in section along the line 2—2.

Referring to FIGS. 1 and 2, a dental mirror 10 is disclosed which comprises a housing 11, a reflector assembly 12 and a motor assembly 13. The housing 11 is typically formed from a non-tarnishing material such as stainless steel, includes a handle 14 and a cord member 15. In the embodiment illustrated in FIGS. 1 and 2, the motion is imparted pneumatically so the handle 14 includes an aperture 16 to accomodate the passage of a fluid; i.e., an air stream. The aperture 16 serially joins a similar aperture in the cord member 15 (not shown) and cooperates with a port-hole 17 and the handle 14. Fluid is supplied through the aperture 16 from a suitable source (not shown).

Figure 3:
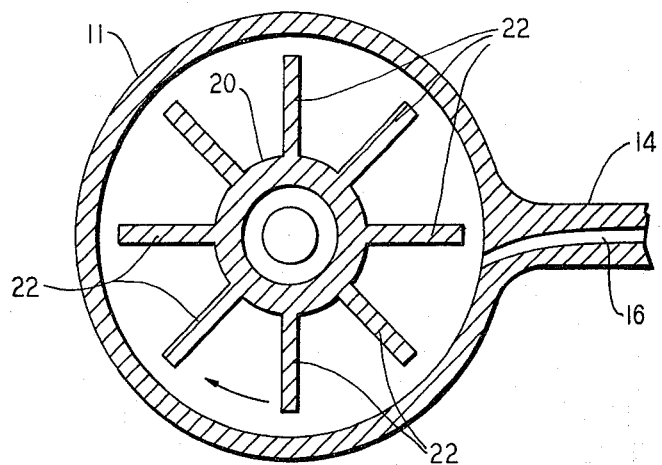
FIG. 3 is a plan view of a portion of the dental mirror shown in FIG. 2 taken partially in section along the line 3—3 and illustrating one form of drive mechanism.

The reflector assembly 12, as shown in FIGS. 2 and 3, comprises a mirror 18, a bearing unit 19, a hub 20 and a turbine 21. The mirror 18 is rigidly attached to the turbine 21 and the bearing unit 19 is affixed to the housing 11 as by riveting or the like. As shown in FIG. 3, the turbine 21 includes blades 22 which pass in front of the interior end of the aperture 16. The bearing unit 19 permits the mirror 18 to rotate when a fluid passes through the aperture 16 and impinges on the blades 22. When the fluid impinging on the blades 22 is air or the like, rotation of the mirror can be controlled by the operator merely by covering and uncovering the port-hole 17. When the mirror 18 rotates fast enough, accumulating moisture is flicked away so as to leave the reflecting function unimpaired.

Figure 4:
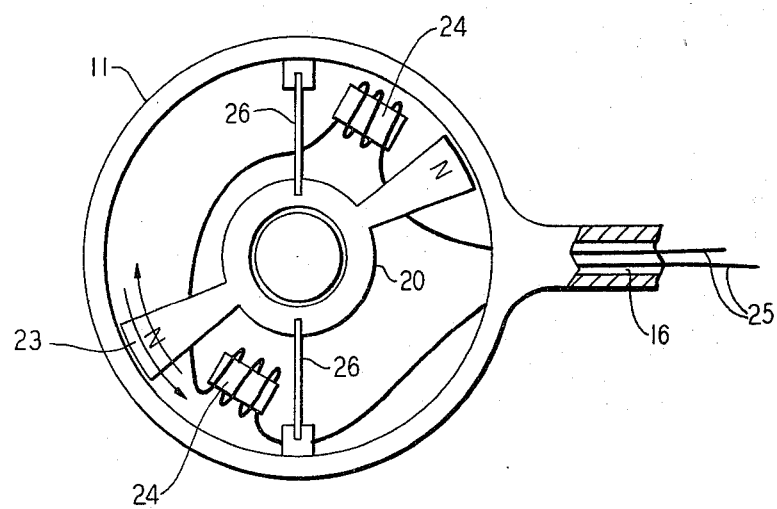
FIG. 4 discloses an alternate form of drive mechanism in the portion of the dental mirror shown in FIG. 3.

The mirror 18 can be driven by alternate means such as the electromagnetic arrangement illustrated in FIG. 4. As shown, the hub 20 includes an armature 23 which cooperates with two electromagnets 24. The electromagnets 24 are energized by wires 25 extending into the housing 11 through the apeture 16. In the embodiment illustrated, the hub 20 is rotationally anchored by a pair of leaf springs 26. In operation, when the electromagnets 24 are energized, the armature 23 is attracted to cause rotation of the hub 20 in one direction. When the electromagnets 24 are de-energized, the leaf springs 26 return the hub to its starting position. When the reciprocation action is rapid enough, the surface of the mirror 18 will be unable to retain moisture droplets thereby maintaining it's reflecting characteristic.

It is also contemplated that the foregoing reciprocating movement can be replaced by complete rotation as by an electric or other type of rotating motor.

In summary, a reflecting device for use in a highly moisturized ambient has been disclosed in which moisture retention on the reflecting surfaces surface is highly retarded. While only preferred embodiments have been disclosed, it will be understood that they are merely exemplary of the principals of the invention and others falling within the scope of the invention will readily occur to those skilled in the art.

What I claim is:

1. A reflecting device for use in a heavily moisturized atmosphere comprising:

housing means adapted for insertion into said highly moisturized atmosphere;

a permanently magnetic armature rotatably mounted on said housing means and being spring biased to reciprocate when magnetically activated;

reflecting means adapted to act as a mirror in said atmosphere, said reflecting means being affixed to said armature, and electro magnetically driven motor means for imparting magnetic actuation to said armature so as to rapidly reciprocate said mirror means in said housing whereby fluid tending to collect on the surface of said mirror is flicked away thereby maintaining the mirror function unimpaired.

* * * * *